(12) United States Patent
Riga et al.

(10) Patent No.: US 8,892,199 B2
(45) Date of Patent: Nov. 18, 2014

(54) CHEMICAL COMPOUND DELIVERY DEVICE AND METHOD

(75) Inventors: Alan T. Riga, Mayfield Heights, OH (US); Vadim F. Lvovich, Cleveland Heights, OH (US); Michael G. Kaufman, Beachwood, OH (US); Thomas I. Bradshaw, Shaker Heights, OH (US)

(73) Assignee: Buckeye Pharmaceuticals, Beachwood, OH (US)

( * ) Notice: Subject to any disclaimer, the term of this patent is extended or adjusted under 35 U.S.C. 154(b) by 1092 days.

(21) Appl. No.: 11/874,859

(22) Filed: Oct. 18, 2007

(65) Prior Publication Data

US 2008/0146986 A1    Jun. 19, 2008

Related U.S. Application Data

(60) Provisional application No. 60/829,978, filed on Oct. 18, 2006.

(51) Int. Cl.
*A61N 1/30* (2006.01)
*A61N 1/32* (2006.01)
*A61N 1/04* (2006.01)

(52) U.S. Cl.
CPC .............. *A61N 1/325* (2013.01); *A61N 1/0436* (2013.01); *A61N 1/044* (2013.01); *A61N 1/303* (2013.01)
USPC ........................................................ 604/20

(58) Field of Classification Search
CPC ....... A61M 1/28; A61M 1/285; A61M 1/287; A61M 2205/18; A61M 2205/582; A61M 2205/6063; A61M 2205/6072; A61M 2205/6081

USPC .................... 604/20, 501; 424/443, 447, 449
See application file for complete search history.

(56) References Cited

U.S. PATENT DOCUMENTS

| 4,734,090 | A | * | 3/1988 | Sibalis ........................... 604/20 |
|---|---|---|---|---|
| 5,240,995 | A | | 8/1993 | Gyory et al. |
| 5,498,235 | A | | 3/1996 | Flower |
| 5,540,669 | A | | 7/1996 | Sage, Jr. et al. |
| 5,958,791 | A | | 9/1999 | Roberts et al. |
| 5,985,316 | A | | 11/1999 | Gyory et al. |
| 6,009,345 | A | | 12/1999 | Hoffmann |
| 6,512,950 | B2 | | 1/2003 | Li et al. |
| 7,133,717 | B2 | | 11/2006 | Coston et al. |

(Continued)

OTHER PUBLICATIONS

Written Opinion of the International Searching Authority (corrected) (Jul. 31, 2009).

(Continued)

*Primary Examiner* — Kami A Bosworth
*Assistant Examiner* — Imani Hayman
(74) *Attorney, Agent, or Firm* — Ulmer & Berne LLP

(57) ABSTRACT

Devices and methods for delivering a chemical compound to, through or into a membrane, tissue or layer are provided. The device may include an AC signal source and at least one electrode. In one application, an interdigitated electrode may be electrically connected to the AC signal source. In one application, the chemical compound such as a medicament containing a drug may be disposed on or within the electrode and logic may control the AC signal source to provide the signal, including setting or selecting characteristics such as voltage, frequency and the like to orient and/or motivate an amount of the chemical compound through the electrode and into the tissue.

11 Claims, 12 Drawing Sheets

(56) References Cited

U.S. PATENT DOCUMENTS

| | | | |
|---|---|---|---|
| 2002/0010414 A1* | 1/2002 | Coston et al. | 604/20 |
| 2005/0148996 A1* | 7/2005 | Sun et al. | 604/501 |
| 2005/0273046 A1 | 12/2005 | Kwiatkowski et al. | |
| 2009/0043346 A1* | 2/2009 | Palti et al. | 607/2 |

OTHER PUBLICATIONS

Finnin, BC et al., "Transdermal Penetration Enhancers; Applications, Limitations, and Potential," Journ. of Pharm. Sci., vol. 88 No. 10, pp. 955-958 (1999).

Riga, A. et al., "Characterization of Organic Surfactants and Dispersants by Frequency-Dependent Dielectric Thermal Analysis and Electrochemistry" from: Materials Characterization by Dynamic and Modulated thermal Analytical Techniques, pp. 157-173, ASTM Stock No. STP 1402.

Pongjanyakul, T. et al., "Shed King Cobra and Cobra Skins as Model Membranes for In-Vitro Nicotine Permeation Studies," J. Pharmacy and Pharmacology, 54, pp. 1345-1350 (2002).

Furness, G., "Global Overview of the Active Transdermal Drug Delivery Market," Drug Delivery, vol. 4 No. 3 (2004).

Pohl, H.A., "Dielectrophoresis," relevant portions from (Tbl. Contents, pp. 6-18, 34-47, 350-355, 467-468), Cambridge University Press (1978).

International Search Report dated Apr. 29, 2008.

Riga, A., et al., "Characterization of Electrorheological Processes by Dielectric Thermal Analysis," 2001 ASTM STP 1402.

Riga, A., et al., "Characterization and Analysis of Pharmaceuticals I. Multiple and In-Tandem Thermal Analytical Techniques," 2003 Amer Pharm Review 6, Issue 1, 110-114.

Malik, H., et al., "Calorimetric and Electrical Properties of a Commercial Transdermal Patch," 2004, Proceedings of the NA Thermal Analysis Society, 32, 417-421, USA.

Kinoshita, T., et al., "Transdermal Delivery of Lidocaine in Vitro by Alternating Current," J Med Dent Sci. 2003, 50:71-77, USA.

Bhasi, K., et al., "Characterization of Snake Skin by Thermoanalytical Techniques," Journal of Thermal Analysis and Calorimetry 2004 75:269-276.

Ramos, A., et al., "AC Electrokinetics: A Review of Forces in Microelectrode Structures," J. Phys. D: Appl. Phys., 31, 1998: 2338-2353.

Morgan, H., et al., "Dielectrophoretic and Travelling Wave Forces Generated Interdigitated Electrode Arrays: Analytical Solution et al., Using Fourier Series," J. Phys. D: Appl. Phys., 34, 2001: 1553-1561.

Burke, P.J., "Nanodielectrophoresis: Electronic Nanotweezers," Encyclopedia of Nanoscience and Nanotechnology, vol. 10, 2003, 1-19.

Gadish, N., et al., "High Throughput Positive-Dielectrophoretic Bioparticle Microconcentrator," Anal. Chem., 78, 2006: 7870-7876.

Tay, F.E.H., et al., "Electrical and Thermal Characterization of a Dielectrophoretic Chip with 3D Electrodes for Cells Manipulation," Electrochimica Acta, 52, 2007: 2862-2868.

Cleary, G., "Transdermal & Transdermal-like Delivery System Opportunities: Today & the Future," Drug Delivery Technology, Jul. 2005.

Langer, R., "Transdermal Drug Delivery: Past Progress, Current Status, and Future Prospects," Advanced Drug Delivery Reviews, 2004, 56:557-558.

Cleary, G., "Transdermal Controlled Release Systems," Medical Applications of Controlled Release, vol. 1, Langer, RS and Wise DL, CRC Press, Inc. Boca Raton, FL, 203-251, 1984.

Chong, S., et al., "Transdermal Drug Delivery Systems: Pharmacokinetics, Clinical Efficacy, and Tolerance Development," Transdermal Drug Delivery, NY 1989:135-153.

Audet, MC., et al., "Eval. of Contraceptive Efficacy and Cycle Control of a Transdermal Contraceptive Patch vs. An Oral Contraceptive: A Randomized Controlled Trial," JAMA 2001, 285(18):2347-2354.

World Health Organization, "Adherance to Long-Term Therapies, Evidence for Action," 2003.

Peveler, R., et al., "Treatment Delivery and Guidelines in Primary Care," British Medical Bulletin, 2001, 57:193-206.

Riga, A., et al., "Dielectric Analysis of Transdermal Patches," Proceedings of the North American Thermal Analysis Society, 30, pp. 102-105, 2002.

Pan, W., et al., "Thermal and Electrochemical Methods: Sensors for Characterization of Biological, Pharmaceutical and Polymeric Nanomaterials," CWRU Nanoscience Symposium, 2004.

* cited by examiner

CHEMICAL COMPOUND DELIVERY DEVICE AND METHOD

PRIORITY

This application claims priority to U.S. provisional application Ser. No. 60/829,978, filed Oct. 18, 2006.

FIELD

The present application relates to methods and devices for the delivery of chemical compounds, including drugs, into or through membranes, including mammalian skin or nails, with the aid of an AC signal.

BACKGROUND

The delivery of chemical compounds across membranes is known in the art, and is primarily a function of the permeability of the membrane to the chemical compound of interest and the presence or absence of a motivating force. Many membranes, including biological tissue (such as skin and nails) are relatively impermeable to a range of chemical compounds. This fact has implications in a number of fields, including but not limited to the field of drug delivery.

Several devices and methods enabling the transport of chemical compounds through membranes and/or tissue are described below.

BRIEF DESCRIPTION OF THE DRAWINGS

In the accompanying drawings, structures are illustrated that, together with the detailed description provided below, describe exemplary embodiments of the claimed invention.

In the drawings and description that follows, like elements are identified with the same reference numerals. The drawings are not to scale and the proportion of certain elements may be exaggerated for the purpose of illustration.

DETAILED DESCRIPTION

Figure 1:
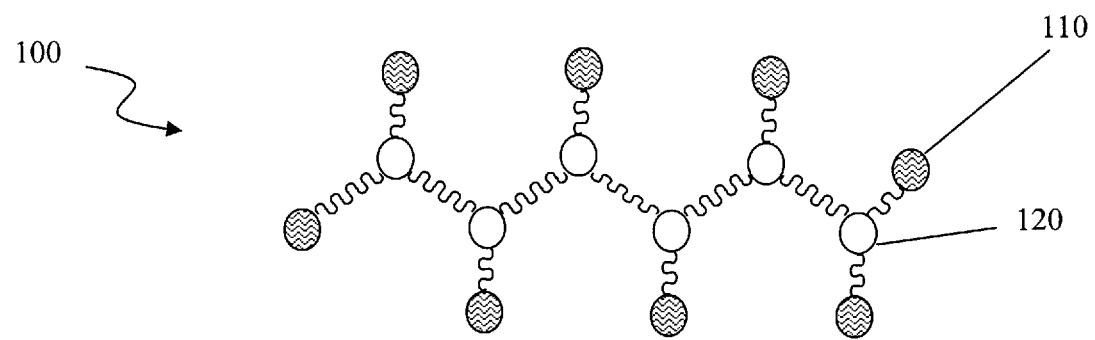
FIG. 1 is a perspective view illustrating a non-polar molecule containing nanosites.

Currently, a need exists for the delivery of chemical compositions including dyes, inks, drugs and other substances across, through or into membranes including natural or synthetic fabrics, biological tissues such as skin or nail tissue, and biological membranes, such as ocular, buccal, mucosal, vaginal, or rectal membranes. With respect to skin, for example, factors such as cell density, tissue thickness and tissue composition make it infeasible to deliver most drugs that are over about 500 Daltons in size without aid of some motivating force. The delivery of compositions into or through nail tissue, tooth enamel, and the like is similarly limited.

The use of an electromotive force to aid transdermal delivery of drugs has been studied. To date, most devices and methods for delivering drugs aided by an electromotive force have involved the use of a simple cathode or anode coupled with a drug source and a DC electrical signal. The use of a DC electrical signal alone, however, may have certain disadvantages, including but not limited to the formation of harmful or undesirable chemical byproducts at the cathode or anode. Moreover, such devices and methods are characterized as "iontophoresis" devices and methods, since they are primarily limited to effecting transport of ionic or strongly polar chemical compounds. Many chemical compounds (including drugs), may not be polar or ionic and/or may be difficult to ionize, rendering the use of iontophoretic devices and methods infeasible on such compounds.

Regarding polarization, many chemical compounds exhibit no dipole (areas of equal charge separated by a distance) in the absence of an electric field because no free charges exist on any site of the compound, or if present the charges are randomly distributed such that no net charge exists on the compound. Such compounds may be polarized and achieve a net dipole if they contain sites capable of being acted upon by an applied electric field. Such sites may comprise any distinct chemical group or moiety within a larger chemical compound that is capable of being attracted or repelled by an applied electric field. The sites are termed "nanosites" when their size is less than about 100 nanometers. Nanosites common to drugs include but are not limited to carbonyl groups, sulfoxide groups, nitro groups, and hydroxide groups.

Unlike iontophoresis, dielectrophoresis is capable of motivating any polarizable chemical compounds, including compounds that are difficult to polarize, such as many drugs and large molecule compositions. Dielectrophoresis involves providing a non-uniform AC or DC electric field to a chemical compound. The non-uniform electric field, in addition to inducing a dipole in a chemical compound, sets up an electrical field gradient that provides an electromotive force on the newly polarized compound, the magnitude and direction of which are dependent on several factors, discussed below.

While not wishing to be bound by any particular theory of mechanism, the following description of underlying dielectrophoretic principles may help illustrate the operation and/or effect of several of the disclosed embodiments. In a non-uniform electric field, the dielectrophoretic force, F, exerted by the field on a polarizable (dielectric) particle, such as a chemical compound, in a surrounding medium may generally be calculated by the equation:

$$F = 2pV\varepsilon_m \text{RE}[K(w)] \text{grad} E_{RMS}^2$$
$$= 2pV\varepsilon_m \text{RE}[(\varepsilon_p^* - \varepsilon_m^*)/(\varepsilon_p^* + 2\varepsilon_m^*)] \text{grad} E_{RMS}^2,$$

where p is the induced dipole moment of the dielectric particle; $E_{RMS}$ is the root mean square value of the non-uniform electric field; V is particle volume; $\epsilon_m$ is the permittivity of the suspending medium; RE[K(w)] is the real part of the "Clausius-Mossotti" factor (in principle, real conductivity); $\epsilon_m^*$ is the complex permittivity of the medium; and $\epsilon_p^*$ is the complex permittivity of the particle. The force may be positive or negative, depending on the relative permittivity values of the particle and the surrounding medium. In general, a positive value ($\epsilon_p^* > \epsilon_m^*$) indicates that the particle will move in a positive direction towards stronger electric field regions, whereas a negative value ($\epsilon_p^* < \epsilon_m^*$) indicates that the particle will move in a negative direction toward weaker electric field regions. The equation applies to both AC and DC fields. Furthermore, since the permittivity values for the dielectric particle and the surrounding medium are dependent on AC signal frequency, the magnitude and direction of the dielectrophoretic force will vary in an AC field depending on frequency. For further discussion of background principles of dielectrophoresis, see H. A. Pohl, Dielectrophoresis, (Cambridge Univ. Press 1978); A. Ramos et al., AC electrokinetics: a review of forces in microelectrode structures, J. Phys. D: Appl. Phys., 31, pp. 2338-23353 (1998); H. Morgan et al., The dielectroiphoretic and traveling wave forces generated by interdigitated electrode arrays: analytical solution using Fourier series, J. Phys. D: Appl. Phys., 34, pp. 1553-1561 (2001); and P. J. Burke, Nanodielectrophoresis: Electronic Nanotweezers, Encycl. Nanoscience and Nanotech., vol. 10, pp. 1-19 (2003).

When the dielectrophoretic force exerted by the field on the polarizable particle is great enough, the particle will move in the surrounding medium, such as carrier vehicle components of a medicament or the tissue to be treated, with a velocity that may generally be calculated by the equation:

$$v = \frac{\sigma E_{RMS}^2 x^2}{a^2} v_{DEP} =$$
$$\frac{\sigma E_{RMS}^2 x^2}{a^3} \frac{F_{DEP}}{6\pi\rho} = \frac{\sigma E_{RMS}^2 x^2}{3\rho} \varepsilon_M \varepsilon_0 \text{RE}\left[\frac{\varepsilon_P^* - \varepsilon_M^*}{\varepsilon_P^* + 2\varepsilon_M^*}\right] \text{grad} E_{RMS}^2$$

Where $\sigma$ is the conductivity of the medium; x is the characteristic size of the electrode; $\rho$ is the viscosity of the media, and $\alpha$ is the size of the polarizable particle (for instance, a drug). The characteristic size of an interdigitated electrode may be approximated by using the distance between two opposing "fingers" on the electrode components.

Non-uniform electric fields may be provided in a number of ways. Generally, utilizing non-uniform electrodes (electrodes having non-uniform geometry) will yield a non-uniform field. For instance, utilizing a pin electrode in combination with a plate electrode yields a non-uniform electric field. Several embodiments of devices disclosed herein utilize an interdigitated electrode ("IDE") arrangement to provide a non-uniform electric field. In general, an IDE is any set of at least two electrodes that contain projections, wherein the projections from each electrode are interwoven with the projections of the other. For example, many IDE's comprise two "comb" electrodes (electrodes having a number of relatively long, flat prongs that are evenly spaced) whose prongs are interleaved.

Regarding the use of dielectrophoresis to transport a polarizable chemical compound through a medium, the chemical compound may be acted upon by a number of forces in addition to the dielectrophoretic force discussed above. For instance, Brownian and electroosmotic forces may act upon the chemical compound. Also, as noted above, when an AC signal is utilized, the magnitude of the dielectrophoretic force exerted upon the chemical compound varies with AC frequency. Thus, it has been found that dielectric analysis, which measures dielectric parameters of a sample (such as permittivity, conductivity, loss factor, impedance and capacitance) at a given frequency, is informative in assessing optimum frequencies to utilize in aiding dielectrophoretic transport of chemical compounds. For instance, using an IDE to generate a non-uniform electric field, it has been observed that, with respect to certain cream-based medicaments, relatively low frequencies may serve to polarize and orient molecules in the medicament, while relatively high frequencies may serve to transport polarized drug molecules in the medicament.

The following includes definitions of selected terms employed herein. The definitions include various examples and/or forms of components that fall within the scope of a term. The examples are not intended to be limiting. Both singular and plural forms of terms may be within the definitions.

"Membrane," "barrier," "barrier membrane," and "tissue" are used interchangeably herein, and include but are not limited to biological membranes and tissues comprising at least one layer of cells or molecules, such as skin or nails, or ocular, buccal, mucosal, vaginal, and rectal membranes.

"Agent," "chemical compound," and "chemical substance" are used interchangeably herein, and include but are not limited to any polar or non-polar molecule or moiety that is capable of exhibiting a dipole moment when exposed to an electric field. The terms include but are not limited to therapeutically effective agents (agents that are capable of having a biological effect), such as pharmaceutical agents or drugs.

"Medicament," as used herein, includes but is not limited to any compound having at least one therapeutically or cosmetically effective agent. Such compounds may include at least one vehicle. "Vehicle," as used herein, includes any non-toxic carrier compositions suitable for administration of an agent across a tissue or membrane.

"Signal," as used herein, includes but is not limited to voltage signals and current signals.

"Logic," as used herein, includes but is not limited to hardware, firmware, software and/or combinations of each to perform a function(s) or an action(s), and/or to cause a function or action from another component. For example, based on a desired application or need, logic may include a software controlled microprocessor, discrete logic such as an application specific integrated circuit (ASIC), a programmed logic device, memory device containing instructions, or the like. Logic may also be fully embodied as software on a computer-readable medium.

The devices and methods disclosed herein may be used in the delivery of a wide range of agents. Generally, the devices and methods may be used to deliver any agent capable of being dielectrophoretically transported into or through a membrane. Often the agent being delivered into or through a membrane is a therapeutically effective agent or a cosmetic agent. Examples of such therapeutically effective agents include but are not limited to ACE inhibitors, steroids, analgesics, anti-coagulants, anti-arthritics, anti-infectives, anti-convulsants, anti-depressives, anti-fungals, anti-hypertensives, anti-psychotics, antihistamines, beta blockers, dermatologics, polypeptides, polynucleotides, NSAIDS, ocular drugs, hormones, and urology drugs. Even more specific examples include but are not limited to ibuprofen, fluoxetine hydrochloride, lidocaine, methrotrexrate, norelgestromin, and insulin, and any derivatives or analogs thereof. An example of a cosmetic agent includes but is not limited to delivery of urea into nails.

Specific examples of anti-fungal agents include but are not limited to amorolfine (dimethylmorpholine), bifonazole, butenafine, butoconazole, clioquinol, ciclopirox olamine, clotrimazole, econazole, fluconazole, griseofulvin, halopro- gen, iodochlorhydroxyquine, itraconazole, ketoconazole, miconazole, naftifine, oxiconazole, povidone-iodine serta- conazole, sulconazole, terbinafine, terconazole, tioconazole, tolnaftate, undecylenic acid and its salts (calcium, copper, and zinc), voriconazole, the sodium or zinc salts of proprionic acid, butylamine, cymoxanil, dodicin, dodine, guazatine, iminoctadine, carpropamid, chloraniformethan, cyflufenamid, diclocymet, ethaboxam, fenoxanil, flumetover, furametpyr, mandipropamid, penthiopyrad, prochloraz, quinazamid, silthiofam, triforine, benalaxyl, benalaxyl-M, furalaxyl, metalaxyl, metalaxyl-M, pefurazoate, benalaxyl, benalaxyl-M, boscalid, carboxin, fenhexamid, metalaxyl, metalaxyl-M, metsulfovax, ofurace, oxadixyl, oxycarboxin, pyracarbolid, thifluzamide, tiadinil, benodanil, flutolanil, mebenil, mepronil, salicylanilide, tecloftalam, fenfuram, furalaxyl, furcarbanil, methfuroxam, flusulfamide, benzohydroxamic acid, fluopicolide, tioxymid, trichlamide, zarilamid, zoxamide, cyclafuramid, furmecyclox, dichlofluanid, tolylfluanid, amisulbrom, cyazofamid, benthiavalicarb, iprovalicarb, aureofungin, blasticidin-S, cycloheximide, griseofulvin, kasugamycin, natamycin, polyoxins, polyoxorim, streptomycin, validamycin, azoxystrobin, dimoxystrobin, fluoxastrobin, kresoxim-methyl, metominostrobin, orysastrobin, picoxystrobin, pyraclostrobin, trifloxystrobin, biphenyl, chlorodinitronaphthalene, chloroneb, chlorothalonil, cresol, dicloran, hexachlorobenzene, pentachlorophenol, quintozene, sodium pentachlorophenoxide, tecnazene, benomyl, carbendazim, chlorfenazole, cypendazole, debacarb, fuberidazole, mecarbinzid, rabenzazole, thiabendazole, furophanate, thiophanate, thiophanate-methyl, bentaluron, chlobenthiazone, TCMTB, bithionol, dichlorophen, diphenylamine, benthiavalicarb, furophanate, iprovalicarb, propamocarb, thiophanate, thiophanate-methyl, benomyl, carbendazim, cypendazole, debacarb, mecarbinzid, diethofencarb, climbazole, imazalil, oxpoconazole, prochloraz, triflumizole, imidazole compounds, azaconazole, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, penconazole, propiconazole, prothioconazole, quinconazole, simeconazole, tebuconazole, tetraconazole, triadimefon, triadimenol, triticonazole, uniconazole, uniconazole-P, triazole compounds, Bordeaux mixture, Burgundy mixture, Cheshunt mixture, copper acetate, copper carbonate, basic, copper hydroxide, copper naphthenate, copper oleate, copper oxychloride, copper sulfate, copper sulfate, basic, copper zinc chromate, cufraneb, cuprobam, cuprous oxide, mancopper, oxine copper, famoxadone, fluoroimide, chlozolinate, dichlozoline, iprodione, isovaledione, myclozolin, procymidone, vinclozolin, captafol, captan, ditalimfos, folpet, thiochlorfenphim, binapacryl, dinobuton, dinocap, dinocap-4, dinocap-6, dinocton, dinopenton, dinosulfon, dinoterbon, DNOC, azithiram, carbamorph, cufraneb, cuprobam, disulfiram, ferbam, metam, nabam, tecoram, thiram, ziram, dazomet, etem, milneb, mancopper, mancozeb, maneb, metiram, polycarbamate, propineb, zineb, cyazofamid, fenamidone, fenapanil, glyodin, iprodione, isovaledione, pefurazoate, triazoxide, conazole compounds (imidazoles), potassium azide, potassium thiocyanate, sodium azide, sulfur, copper compounds, inorganic mercury compounds, mercuric chloride, mercuric oxide, mercurous chloride, (3-ethoxypropyl)mercury bromide, ethylmercury acetate, ethylmercury bromide, ethylmercury chloride, ethylmercury 2,3-dihydroxypropyl mercaptide, ethylmercury phosphate, N-(ethylmercury)-p-toluenesulphonanilide, hydrargaphen, 2-methoxyethylmercury chloride, methylmercury benzoate, methylmercury dicyandiamide, methylmercury pentachlorophenoxide, 8-phenylmercurioxyquinoline, phenylmercuriurea, phenylmercury acetate, phenylmercury chloride, phenylmercury derivative of pyrocatechol, phenylmercury nitrate, phenylmercury salicylate, thiomersal, tolylmercury acetate, aldimorph, benzamorf, carbamorph, dimethomorph, dodemorph, fenpropimorph, flumorph, tridemorph, ampropylfos, ditalimfos, edifenphos, fosetyl, hexylthiofos, iprobenfos, phosdiphen, pyrazophos, tolclofosmethyl, triamiphos, decafentin, fentin, tributyltin oxide, carboxin, oxycarboxin, chlozolinate, dichlozoline, drazoxolon, famoxadone, hymexazol, metazoxolon, myclozolin, oxadixyl, vinclozolin, barium polysulfide, calcium polysulfide, potassium polysulfide, sodium polysulfide, furametpyr, penthiopyrad, boscalid, buthiobate, dipyrithione, fluazinam, fluopicolide, pyridinitril, pyrifenox, pyroxychlor, pyroxyfur, bupirimate, cyprodinil, diflumetorim, dimethirimol, ethirimol, fenarimol, ferimzone, mepanipyrim, nuarimol, pyrimethanil, triarimol, fenpiclonil, fludioxonil, fluoroimide, ethoxyquin, halacrinate, 8-hydroxyquinoline sulfate, quinacetol, quinoxyfen, benquinox, chloranil, dichlone, dithianon, chinomethionat, chlorquinox, thioquinox, ethaboxam, etridiazole, metsulfovax, octhilinone, thiabendazole, thiadifluor, thifluzamide, methasulfocarb, prothiocarb, ethaboxam, silthiofam, anilazine, amisulbrom, bitertanol, fluotrimazole, triazbutil, conazole compounds (triazoles), bentaluron, pencycuron, quinazamid, acibenzolar, acypetacs, allyl alcohol, benzalkonium chloride, benzamacril, bethoxazin, carvone, chloropicrin, DBCP, dehydroacetic acid, diclomezine, diethyl pyrocarbonate, fenaminosulf, fenitropan, fenpropidin, formaldehyde, furfural, hexachlorobutadiene, iodomethane, isoprothiolane, methyl bromide, methyl isothiocyanate, metrafenone, nitrostyrene, nitrothal-isopropyl, OCH, 2-phenylphenol, phthalide, piperalin, probenazole, proquinazid, pyroquilon, sodium orthophenylphenoxide, spiroxamine, sultropen, thicyofen, tricyclazole, iodophor, silver, Nystatin, amphotericin B, griseofulvin, and zinc naphthenate, and any derivatives or analogs thereof.

FIG. 1 illustrates a perspective view of a non-polar molecule 100 containing nanosites 110 and 120. Molecule 100 contains no dipole since its nanosites, including nanosites 110 and 120, exhibit no free charge. In general, whether a nanosite exhibits free charge depends upon a number of factors, including but not limited to the composition of the nanosite and the surrounding medium.

Figure 2:
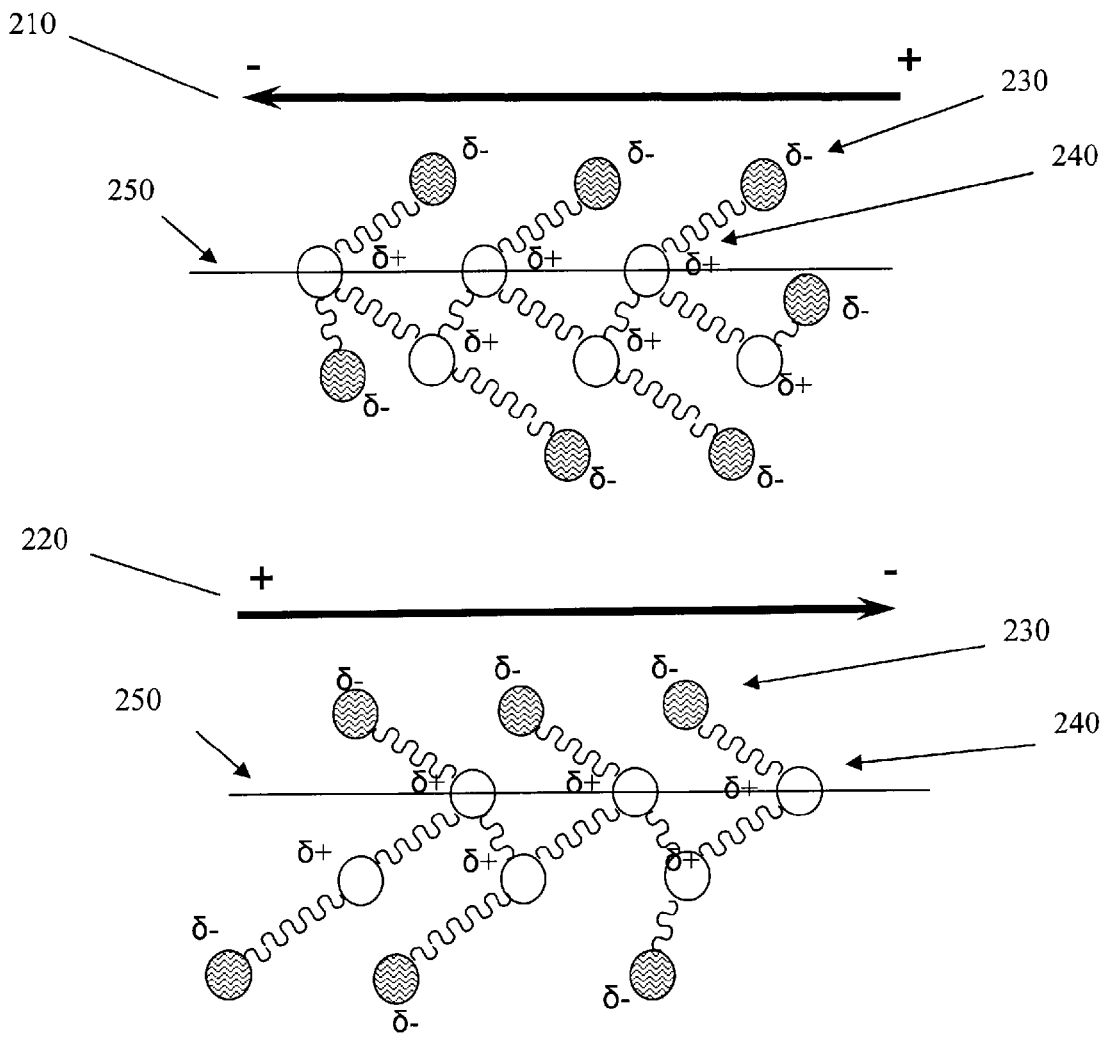
FIG. 2 is a perspective view illustrating a non-polar molecule containing nanosites that is acted upon by an AC electric field.

FIG. 2 illustrates a perspective view of the same non-polar molecule that is acted upon by an AC electric field, represented by opposing field vectors 210 and 220. In an AC field, field vectors 210 and 220 change direction with frequency characterized by the frequency of the AC power signal that is supplied to the area. The magnitude of field vectors 210 and 220 (indicative of the strength of the electric field) depends on a number of factors, including but not limited to the amplitude of the power signal. Field vectors 210 and 220 exhibit attract or repel nanosites 230 and 240, causing then to orient in the field, and the collective effect of such forces on every nanosite causes a net dipole 250 to set up in the molecule. Such dipoles may effect movement of the molecule in a non-uniform electric field, as discussed above.

Figure 3:
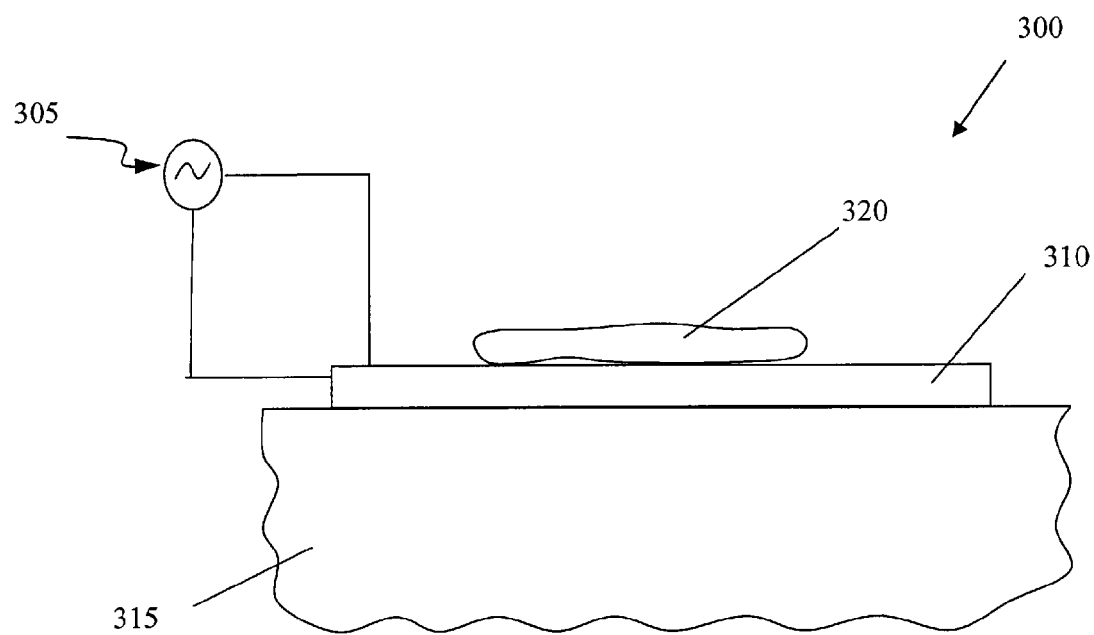
FIG. 3 is a side sectional view illustrating one embodiment of a device for delivering a drug to a tissue.

FIG. 3 illustrates a side sectional view of one embodiment of a device 300 for delivering a drug to a tissue. In one embodiment, an AC signal source 305 capable of providing an AC signal having certain characteristics is electrically connected to electrode 310. Electrode 310 may be any non-uniform or irregularly shaped electrode capable of providing a non-uniform electric field to an area sufficient to induce dielectrophoretic transport and that contains at least one passage sufficient to allow an amount of medicament 320 to pass therethrough. The electrode 310 may be disposed on tissue 315. Tissue 315 may include any tissue, including but not limited to skin, nail, tooth enamel and ocular tissue. Medicament 320 may be disposed onto electrode 310 on the face opposite tissue 315. Alternatively, medicament 320 may be located under or embedded within electrode 310. Medicament 320 may generally include any therapeutic or cosmetic compound having a polarizable active agent, including but not limited to ibuprofen, fluoxetine hydrochloride, ketoconazole, norelgestromin, terbinafine hydrochloride, and insulin. Medicament 320 may optionally include at least one inert vehicle. An example of a medicament having an active agent and vehicle is Lamisil AT. Discussion of medicament formulation generally may be found in the latest edition of *Remington's Pharmaceutical Sciences* (Mack Publ.).

Figure 4:
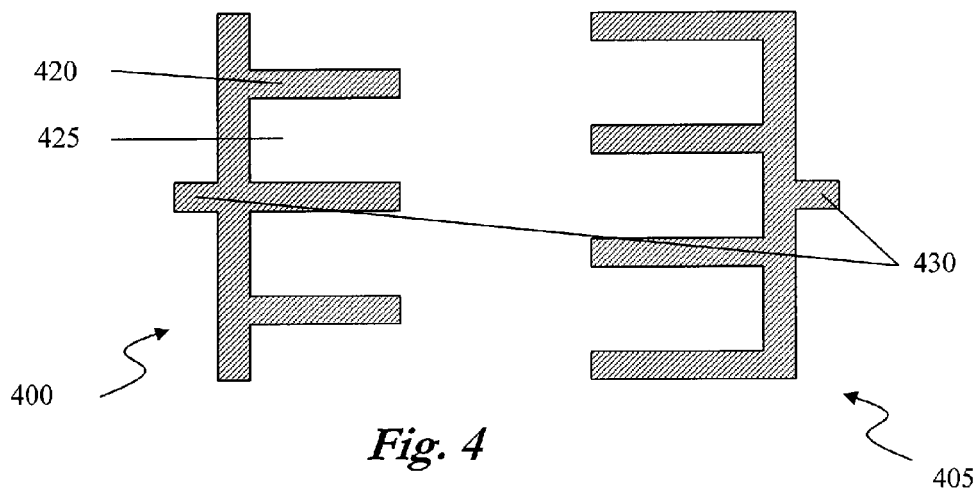
FIG. 4 is a perspective view illustrating one embodiment of irregularly-shaped, component electrodes for an interdigitated electrode.

Referring now to FIG. 4, the non-uniform electrode may be arranged as an interdigitated electrode comprising complementary, irregularly-shaped "comb"-type electrodes 400 and 405 that each contain a number of fingers 420 separated by interstitial areas 425. The dimensions of fingers 420 may generally permit a finger 420 to be longer than its width. Complementary electrodes 400 and 405 may be made of any suitable conducting material. In one embodiment, complementary electrodes 400 and 405 are made of stainless steel. In another embodiment, the electrodes may be made of gold-plated copper. In another embodiment, complementary electrodes 400 and 405 have material composition and dimensions that allow for substantial flexibility and conformability.

Figure 5:
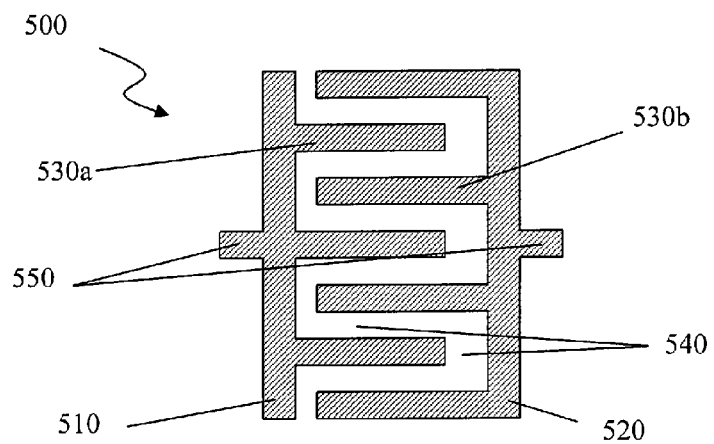
FIG. 5 is a perspective view illustrating one embodiment of an interdigitated electrode.

Referring now to FIG. 5, interdigitated electrode 500 is comprised of irregularly-shaped component electrodes 510 and 520 that are arranged in a coplanar manner where fingers 530a from component electrode 510 interleave fingers 530b of component electrode 520, and where interstitial areas 540 remain between the fingers 530a,b and between the tips of each finger and the body of the component electrodes. Interstitial areas 540 may be varied substantially. In one embodiment, interstitial areas 540 are each on the order of 0.1 mm. Component electrodes 510 and 520 each have an electrical connector 550 that allows for electrical connectivity to an electrical signal source (not shown). In another embodiment, interdigitated electrode 500 may be etched or otherwise formed on a printed circuit board.

Figure 6:
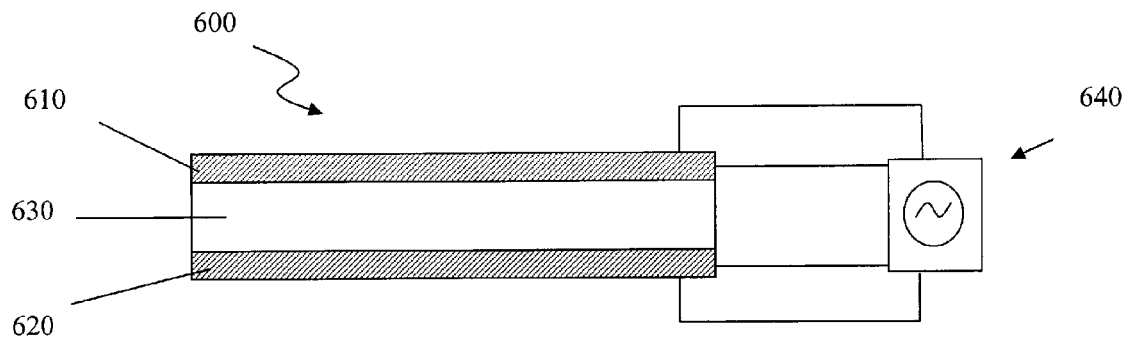
FIG. 6A is a side sectional view illustrating one embodiment of an interdigitated electrode arrangement.
FIG. 6B is a perspective view illustrating one embodiment of an interdigitated electrode arrangement.

FIG. 6A illustrates a side sectional view of one embodiment of an arrangement of non-uniform electrodes according to the present application interdigitated electrode arrangement 600. Interdigitated electrode arrangement 600 includes first and second interdigitated electrodes 610 and 620, each of which may be electrically connected to an AC signal source 640. The electrodes may be spaced apart by insulator 630 made of any insulating material suitable for use in designing an arrangement of electrodes and/or circuits, including but not limited to fiberglass and teflon. In one embodiment, interdigitated electrodes 610 and 620 are identical to each other. In another embodiment, interdigitated electrodes 610 and 620 and insulator 630 have interstitial areas (not shown) that facilitate movement of medicament or other compositions therethrough. In another embodiment, the interstitial areas substantially overlap, forming a passage extending from the top face of first interdigitated electrode 610 to the bottom face of interdigitated electrode 620, with a width sufficient to allow an amount of medicament or other composition to pass therethrough.

FIG. 6B illustrates a perspective view of interdigitated electrode arrangement 600, showing the irregularly-shaped component electrodes of interdigitated electrodes 610 and 620. In this embodiment, the irregularly-shaped component electrodes are "comb"-type electrodes. In particular, interdigitated electrode 610 is comprised of first and second irregularly-shaped component electrodes 611 and 612. Interdigitated electrode 620 is comprised of third and fourth irregularly-shaped component electrodes 621 and 622. AC signal source 640 may selectively apply a signal to a selected one of the first and second interdigitated electrodes 610 and 620 establishing a field between the component electrodes (i.e., between first and second irregularly-shaped electrodes 611 and 612, and/or between third and fourth irregularly-shaped electrodes 621 and 622) or to both the first and second interdigitated electrodes 610 and 620 establishing a field between the first and second interdigitated electrodes 610 and 620. In an alternative embodiment, the component electrodes of first and second interdigitated electrode 610 and 620 may be shorted, allowing first interdigitated electrode 610 to function as a single electrode and second interdigitated electrode 620 to function as a single electrode. In an alternative embodiment, AC signal source 640 may selectively apply a DC offset voltage to a selected one of the first and second interdigitated electrodes 610 and 620. In an alternative embodiment, a DC signal source (not shown) may selectively apply a DC signal to one or both of the first and second interdigitated electrodes.

Figure 7:
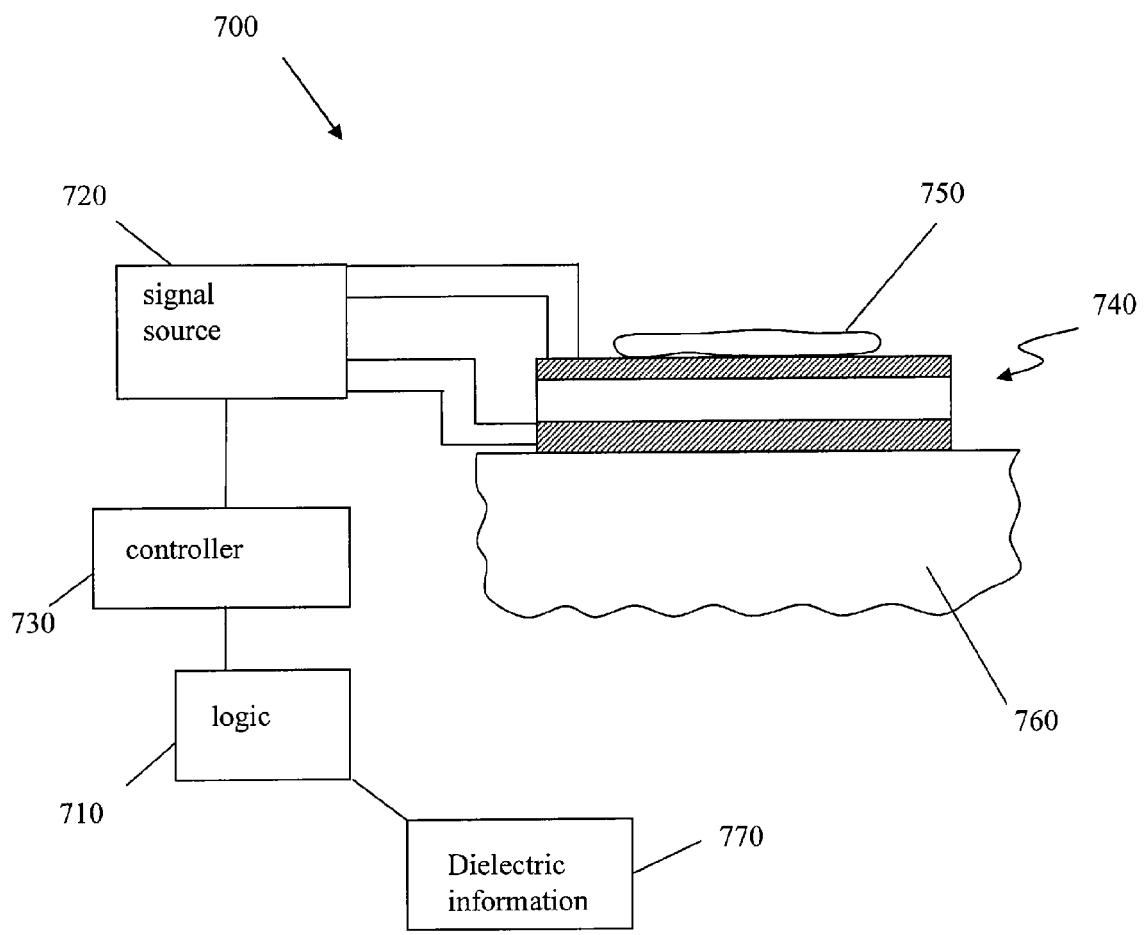
FIG. 7 is a perspective view illustrating one embodiment of a device for orienting and urging a drug to a tissue.

Referring now to FIG. 7, a device 700 for orienting and urging a drug to a tissue includes logic 710 configured to control AC signal source 720, where the logic causes controller 730 to select an AC signal to be applied to electrode arrangement 740 in order to orient molecules contained in medicament 750 and to motivate them through the electrode arrangement 740 and into tissue 760. Tissue 760 includes but is not limited biological tissues such as skin or nail tissue, and biological membranes, such as ocular, buccal, mucosal, vaginal, or rectal membranes. Electrode arrangement 740 comprises at least one non-uniform electrode. In one embodiment, electrode arrangement 740 may be an interdigitated electrode arrangement. In another embodiment, electrode arrangement 740 may be a printed circuit board. In one embodiment, a first signal may orient the molecules in medicament 750 while a second signal may motivate the molecules through electrode arrangement 740 and into tissue 760.

Again referring to FIG. 7, in one embodiment logic 710 may be configured to monitor and record current and phase data from electrode arrangement 740 and to calculate dielectric information 770 regarding medicament 750 as a function of AC signal frequency. Dielectric information 770 may include, but is not limited to, capacitance, conductance, permittivity ($\epsilon'$), dielectric loss factor ($\epsilon''$), and impedance information. Dielectric information 770 may be plotted or stored as a function of AC signal frequency in order to allow for the selection of appropriate operating frequencies for device 700 that will allow for drug molecules in medicament 750 to be oriented or to be motivated through electrode arrangement 740 and into tissue 760.

Again referring to FIG. 7, appropriate operating frequencies may be determined in a number of ways using dielectric information 770. In one embodiment, dielectric data is analyzed to determine a characteristic frequency that delineates a range of relatively high operating frequencies for motivating medicament 750 from a range of relatively low operating frequencies for orienting molecules in medicament 750. In one embodiment, the characteristic frequency is identified by collecting conductivity information spanning a number of decades of frequencies, plotting the log of conductivity against the log of frequency, fitting two lines of different slopes to the data, and choosing as a characteristic frequency the extrapolated frequency value corresponding to the intersection of the two fitted lines. The characteristic frequency value is dependent on a number of factors, including the identity of medicament 750 and the design of electrode arrangement 740. In one embodiment, medicament 750 is Lamicil AT cream, electrode arrangement 740 is a single surface interdigitated electrode, and the extrapolated frequency value is between 10 Hz and 100 Hz.

Again referring to FIG. 7, in another embodiment a relatively high (motivating) operating frequency is selected by collecting dielectric information spanning several decades of frequencies and plotting either conductivity or impedance against frequency (or the log of frequency) and thereafter selecting as a high operating frequency a frequency value where conductivity is relatively high and constant, or the impedance is relatively low and constant. In one embodiment, a relatively high operating frequency is selected to be between about 100 Hz and about 20,000 Hz. In another embodiment, a relatively low (orienting) operating frequency is selected by collecting dielectric information spanning several decades of frequencies and plotting capacitance against frequency (or the log of frequency) and thereafter selecting as a low operating frequency a frequency value where capacitance is relatively high and constant. In one embodiment, a relatively low operating frequency is selected to be between about 0.1 Hz and about 100 Hz.

Again referring to FIG. 7, in one embodiment logic 710 applies first and second AC signals to electrode arrangement 740, where the first signal is at a relatively low frequency selected to orient molecules, including drug molecules, in medicament 750 and the second signal is at a relatively high frequency selected to motivate drug molecules in medicament 750 into tissue 760. In another embodiment, logic 710 causes AC signal source 720 to apply a first (AC) signal to electrode arrangement 740 sufficient to orient molecules in medicament 750 and causes a DC signal source (not shown) to apply a second (DC) signal to electrode arrangement 740 in order to motivate medicament 750 into tissue 760.

Figure 8:
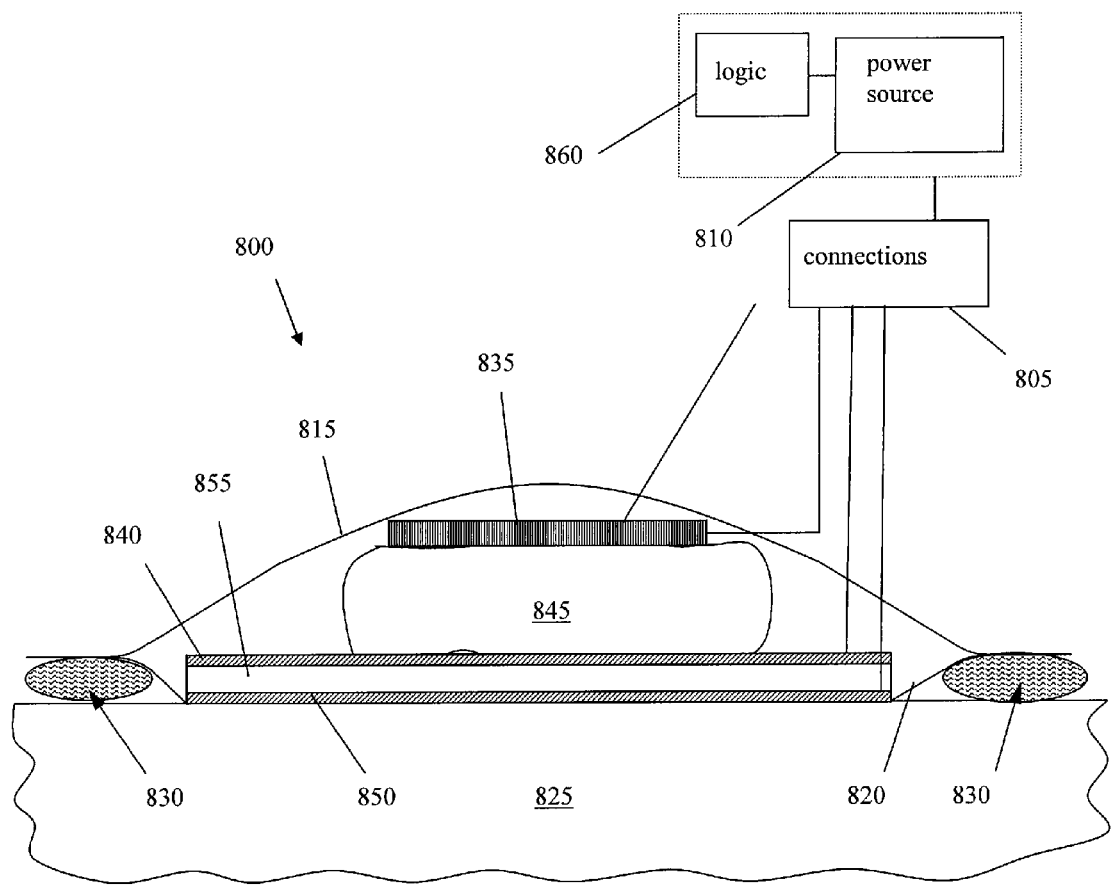
FIG. 8 is a side sectional view illustrating one embodiment of a transdermal patch for delivering a drug through tissue.

FIG. 8 illustrates a side sectional view of one embodiment of a transdermal patch 800 for delivering a drug through tissue 825. Transdermal patch 800 includes electrical connections 805 for receiving an electrical signal from an electrical power source 810. Transdermal patch 800 also includes a bandage having a distal layer 815 and a proximate layer 820. Various commercially available bandages suitable for use in transdermal patches may be modified to include the components discussed below. Transdermal patch 800 may be adapted to allow proximate layer 820 to adhere to tissue 825. Tissue 825 includes but is not limited biological tissues such as skin or nail tissue, tooth enamel, and biological membranes, such as ocular, buccal, mucosal, vaginal, or rectal membranes. Any suitable means for adhering transdermal patches to tissue may be used. In one embodiment, transdermal patch 800 is designed such that it includes a periphery of adhesive 830 suitable for adhesion to skin tissue. In another embodiment, the patch may be physically or mechanically held adjacent tissue 825. Transdermal patch 800 includes a distal electrode 835 disposed internal to the patch and adjacent the distal layer 815. The distal electrode may be electrically connectable to at least one of the connections 805. At least one non-uniform electrode 840 is disposed proximally thereto and may also be electrically connectable to connections 805. In one embodiment, non-uniform electrode 840 is an interdigitated electrode.

A medicament 845 may be disposed onto non-uniform electrode 840 opposite tissue 825. As discussed, medicament 845 may generally be any therapeutic compound having at least one polarizable drug. Medicament 845 may optionally have at least one inert carrier vehicle. In an alternative embodiment (not shown), medicament 845 is formulated to be an adhesive. In another embodiment, medicament 845 is an adhesive identical to adhesive 830. In another embodiment, non-uniform electrode 840 is configured to allow an amount of medicament 845 to pass therethrough.

In one embodiment an AC electrical signal may be applied to connections 805 and to non-uniform electrode 840, the signal being sufficient to cause drug in medicament 845 to orient in a desired manner. In one embodiment, the electrical signal may be an AC signal with a frequency within about 0.1 Hz to about 100 Hz. In another embodiment, an AC electrical signal may be applied to connections 805, to distal electrode 835 and to non-uniform electrode 840, the signal being sufficient to motivate an amount of drug in medicament 845 through non-uniform electrode 840. In one embodiment, the electrical signal may be an AC signal with a frequency between about 100 Hz and about 20,000 Hz. Transdermal patch 800 may include a second non-uniform electrode 850 configured to allow an amount of medicament to pass therethrough. In one embodiment, non-uniform electrode 850 is an interdigitated electrode. Second non-uniform electrode 850 may be electrically connectable to connections 805 and spaced apart from non-uniform electrode 840 by insulating layer 855. In one embodiment, an electrical signal may be applied to connections 805 and to second non-uniform electrode 850 that is sufficient to motivate an amount of drug in medicament 825 through second non-uniform electrode 850 and into tissue 845. In one embodiment, the electrical signal may be an AC signal with a frequency between about 100 Hz and about 20,000 Hz.

Again referring to FIG. 8, in one embodiment, logic 860 causes power source 810 to apply an AC signal to connection 805 sufficient to motivate an amount of drug in medicament 825 through second non-uniform electrode 850 and into tissue 845. In another embodiment, logic 860 is configured to switch power source 810 on and off depending on a predetermined dosing schedule. In an another embodiment, a sensor (not shown) in communication with tissue 825 monitors a condition of tissue 825, such as impedance or conductivity, and logic 860 is configured to switch power source 810 on and off depending on the monitored condition. In another embodiment, logic 860 adjusts the frequency applied to connection 805 based on the monitored condition. In another embodiment, logic 860, power source 810, and connections 805 are contained within the bandage.

Figure 9:
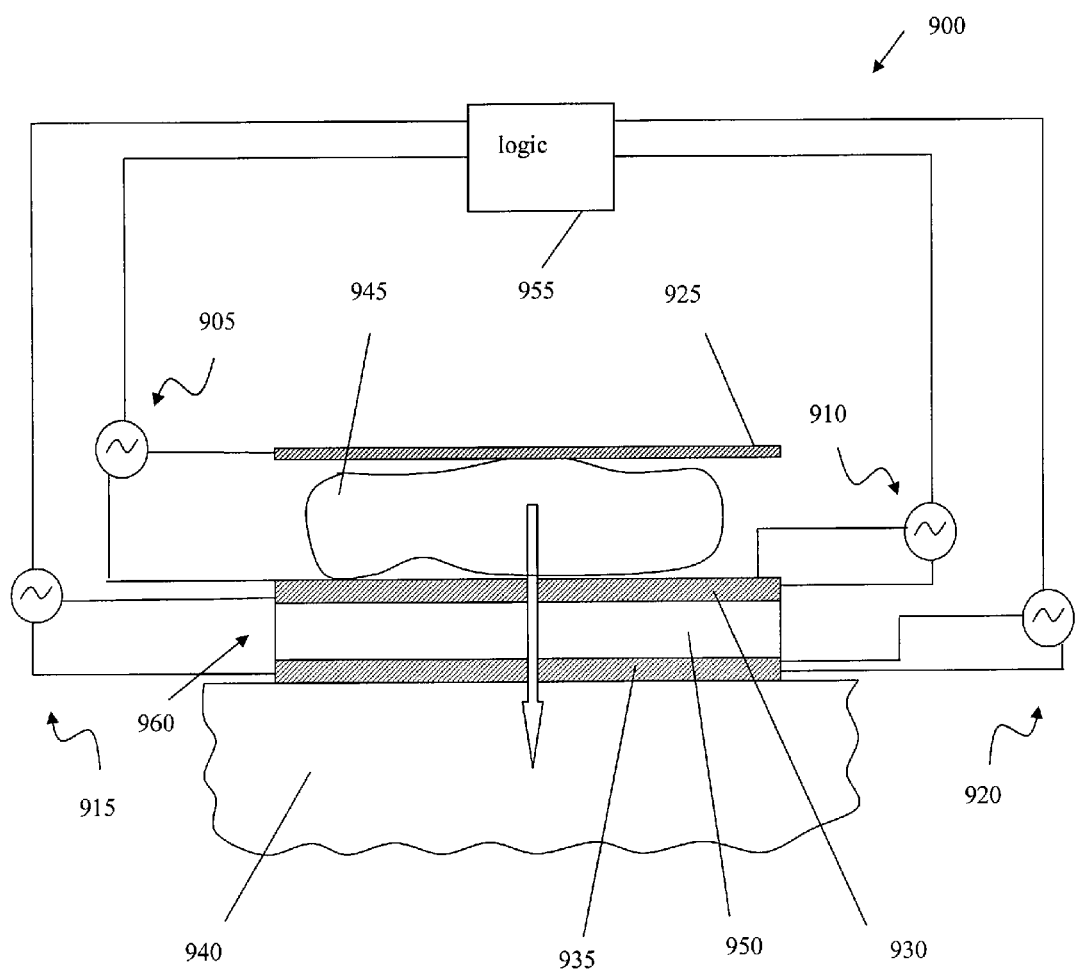
FIG. 9 is a side sectional view illustrating one embodiment of a device for urging a chemical substance through a membrane.

FIG. 9 is a side sectional view of one embodiment of a device 900 for urging a chemical substance through or into a membrane. Device 900 includes first AC power source 905, second AC power source 910, third AC power source 915, and fourth AC power source 920. Each AC power source has a first terminal and a second terminal (not shown). Electrode 925 is electrically connected to the first terminal of first AC power source 905. Electrode 925 may generally be designed from any suitable conductive material and in any suitable geometry, including but not limited to a plate design. First interdigitated electrode 930 is electrically connected to the second terminal of first AC power source 905 and to the first and second terminals of second AC power source 910, and to the first terminal of third AC power source 915. Second interdigitated electrode 935 is electrically connected to the second terminal of third AC power source 915 and to the first and the second terminals of fourth AC power source 920. First interdigitated electrode 930 is disposed between second interdigitated electrode 935 and electrode 925. Second interdigitated electrode 935 is disposed between first interdigitated electrode 930 and membrane 940. Membrane 940 includes but is not limited biological tissues such as skin or nail tissue, tooth enamel, and biological membranes, such as ocular, buccal, mucosal, vaginal, or rectal membranes. First and second electrodes 930 and 935 and insulating layer 950 comprise electrode arrangement 960.

Again referring to FIG. 9, an amount of chemical compound 945 is disposed between electrode 925 and first interdigitated electrode 930. Chemical compound 945 may be generally any polarizable chemical compound, including but not limited to a drug (including but not limited to ibuprofen, fluoxetine hydrochloride, ketoconazole, norelgestromin, terbinafine hydrochloride, and insulin) or medicament comprising a drug (including but not limited to Lamicil AT).

Again referring to FIG. 9, logic 955 is employed to control first AC power source 905, second AC power source 910, third AC power source 915, and fourth AC power source 920. For purposes of analysis and description, equivalent circuits are described. The application of electrical signal to electrode 925 and first interdigitated electrode 930, in the presence of chemical compound 945, is referred to as "Circuit 1." It is noted here that first and second interdigitated electrode 930 and 935, respectively, are comprised of component electrodes (not shown), examples of which were discussed. The component electrodes of first interdigitated electrode 930 may optionally be shorted, such that, in relation to Circuit 1, interdigitated electrode 930 functions as a single electrode. The application of electrical signal to the component electrodes of first interdigitated electrode 930, in the presence of chemical compound 945, is referred to as "Circuit 2." The application of electrical signal to first and second interdigitated electrodes 930 and 935, in the presence of chemical compound 945, is referred to as "Circuit 3." The component electrodes of first and second interdigitated electrodes 930 and 935 may optionally be shorted, such that, in relation to Circuit 3, interdigitated electrodes 930 and 935 each function as single electrodes. Finally, the application of electrical signal to the component electrodes of second interdigitated electrode 935, in the presence of chemical compound 945, is referred to as "Circuit 4."

In one embodiment, logic 955 causes first AC power source 905 and third AC power source 915 to supply a relatively high frequency signal to Circuits 1 and 3 in order to motivate medicament 945 toward tissue 940 and into tissue 940. In another embodiment, logic 955 causes second AC power source 910 and fourth AC power source 920 to supply a relatively low frequency signal to Circuits 2 and 4 in order to orient a drug in medicament 945 in relation to the electric field generated by interdigitated electrodes 930 and 935. Methods for selecting appropriate high and low frequencies were discussed. In one embodiment, the high frequency signal is between about 100 Hz and 20,000 Hz and the low frequency signal is between about 0.1 Hz and 100 Hz. In another embodiment, logic 955 causes AC signals to be supplied to Circuits 1-4 in a successive manner. In another embodiment, logic 955 causes AC signals to be supplied to Circuits 1-4 simultaneously. In another embodiment, logic 955 is configured to switch power source 905 on and off depending on a pre-determined dosing schedule. In an another embodiment, a sensor (not shown) in communication with tissue 940 monitors a condition of tissue 940, such as impedance or conductivity, and logic 955 is configured to switch power source 905 on and off depending on the monitored condition. In another embodiment, logic 955 adjusts frequency in any of Circuits 1-4 based on the monitored condition. In another embodiment, electrode arrangement 960 comprises a printed circuit board.

Figure 10:
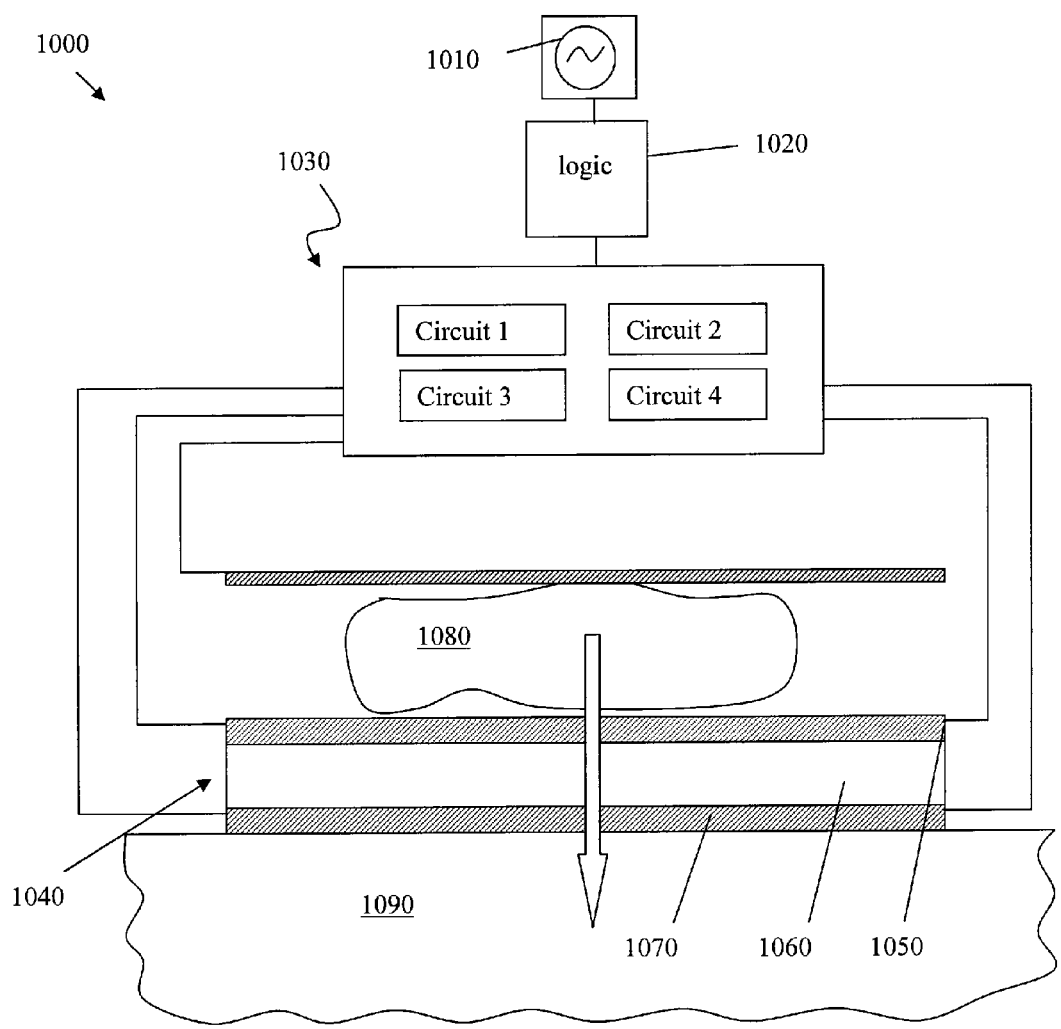
FIG. 10 is a side sectional view illustrating one embodiment of a device for urging a chemical substance through a porous surface.

FIG. 10 is a side sectional view of one embodiment of a device 1000 for urging a chemical substance 1080 through or into a porous surface 1090. Chemical substance 1080 may be generally any polarizable chemical compound, such as paint, stain, ink, conditioner and the like.

Device 1000 may include single AC power source 1010. Switching means 1030 permits single AC power source 1010 to supply a signal to selected or every electrode in device 1000 (i.e., to each Circuit 1-4). Logic 1020 may be coupled with switching means 1030 and may cause pre-selected frequencies to be supplied by single AC power source 1010 to any of Circuits 1-4. Device 1000 may also include an arrangement of interdigitated electrodes 1040. Arrangement 1040 includes a planar first interdigitated electrode 1050 having a thickness, a planar insulating layer 1060 having a top and bottom face and a thickness, and a planar second interdigitated electrode 1070 having a thickness. Insulating layer 1060 may be any insulating material suitable for use in electronic circuits. The bottom face of the first interdigitated electrode 1050 may be attached to the top face of insulating layer 1060 and the bottom face of insulating layer 1060 may be attached to the top face of second interdigitated electrode 1070. In an embodiment, at least one gap (not shown) having a width sufficient to allow an amount of chemical substance 1080 to pass therethrough extends from the top face of first interdigitated electrode 1050 through the bottom face of second interdigitated electrode 1070 and into the porous surface 1090.

In one embodiment, logic 1020 causes a relatively high frequency signal to be supplied to Circuits 1 and 3 in order to motivate chemical substance 1080 into porous surface 1090. In another embodiment, logic 1020 causes a relatively low frequency signal to be supplied to Circuits 2 and 4 in order to orient chemical substance 1080 in relation to the electric field generated by interdigitated electrodes 1050 and 1070. In one embodiment, the high frequency signal is between about 100 Hz and about 20,000 Hz and the low frequency signal is between about 0.1 Hz and about 100 Hz. In another embodiment, logic 1020 causes AC signals to be supplied to Circuits 1-4 in a successive manner. In another embodiment, logic 1020 causes AC signals to be supplied to Circuits 1-4 simultaneously. In another embodiment, logic 1020 is configured to switch power source 1010 on and off depending on a pre-determined dosing schedule. In an another embodiment, a sensor (not shown) in communication with porous surface 1090 monitors a condition of the surface 1090, such as impedance or conductivity, and logic 1020 is configured to switch power source 1010 on and off depending on the monitored condition. In another embodiment, logic 1020 adjusts frequency in any of Circuits 1-4 based on the monitored condition. In another embodiment, electrode arrangement 1040 comprises a printed circuit board.

Again referring to FIG. 10, in one embodiment logic 1020 may cause signals on Circuits 1-4 to each be of different frequencies and/or voltages. In another embodiment, logic 1020 may cause signals on Circuits 1 and 3 to operate at a first frequency and signals operating on Circuits 2 and 4 to operate at a second frequency. In another embodiment, logic 1020 may cause signals on Circuits 1 and 3 to operate at a frequency between about 100 Hz and about 20,000 Hz and may cause signals on Circuits 2 and 4 to operate at a frequency between about 0.1 Hz and about 100 Hz.

Figure 11:
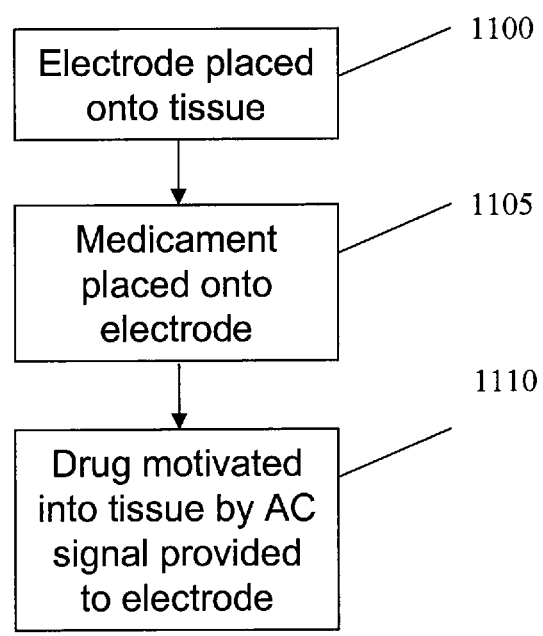
FIG. 11 is a flowchart illustrating one embodiment of a method for delivering a drug to tissue.

FIG. 11 illustrates an embodiment of a method for delivering a drug to a tissue. A user first places a non-uniform electrode that is electrically connected to an AC signal source onto tissue selected for treatment or selected as a site for delivering a drug, step 1100. In one embodiment, the non-uniform electrode is an interdigitated electrode. In another embodiment, the non-uniform electrode is a printed circuit board. An amount of medicament including at least one drug is then placed onto the non-uniform electrode, step 1105, and the AC source provides a signal with a frequency sufficient to motivate an amount of the drug into the tissue, step 1110. In one embodiment, the drug is terbinafine hydrochloride and the AC signal frequency is between about 0.1 Hz and about 20,000 Hz.

Figure 12:
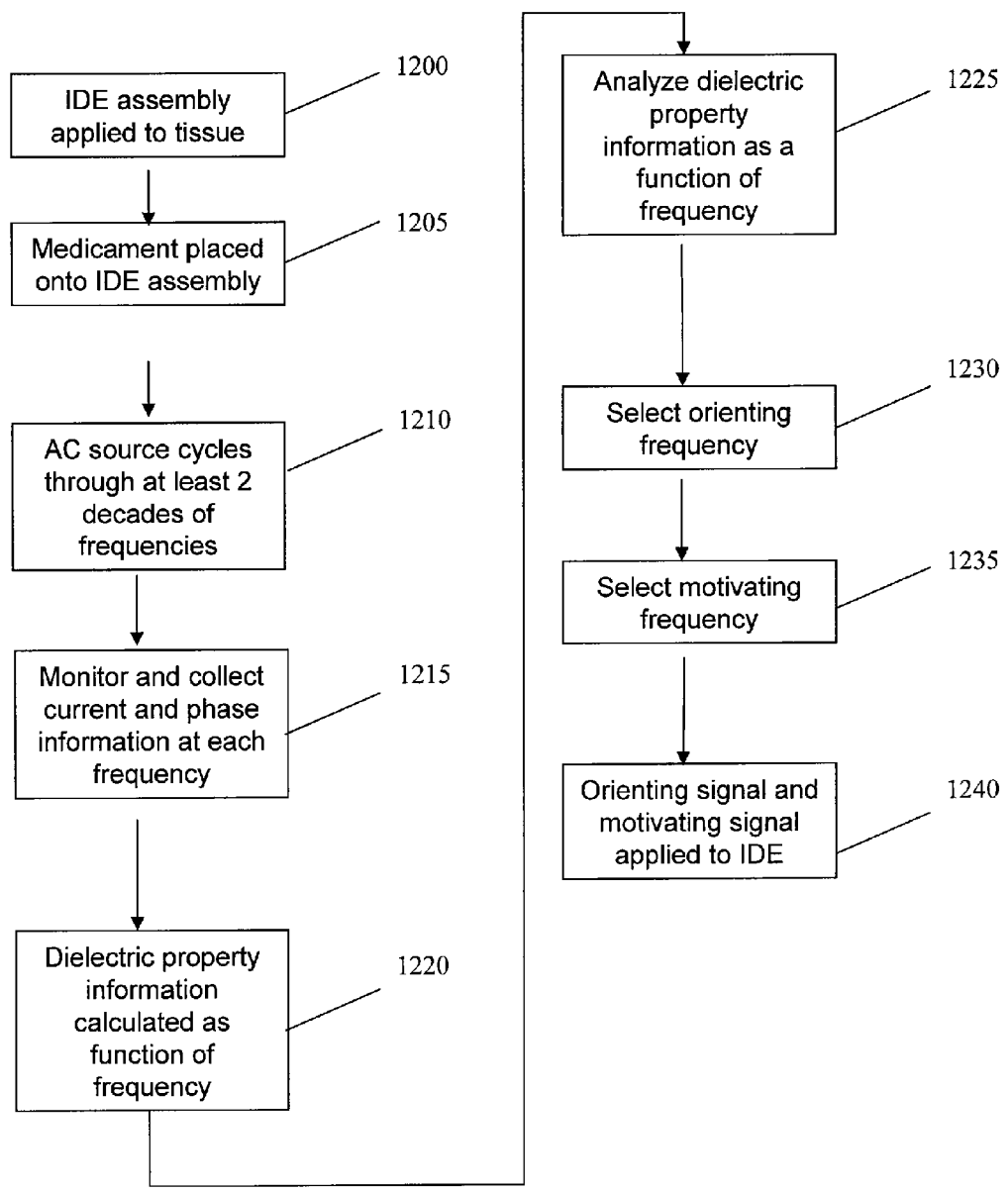
FIG. 12 is a flowchart illustrating one embodiment of a method for delivering a drug to tissue.

FIG. 12 illustrates an embodiment of a method for delivering a drug to a tissue. A user first places an interdigitated electrode assembly that is electrically connected to an AC signal source onto tissue selected for treatment or selected as a site for delivering a drug, step 1200. The interdigitated electrode assembly may be an arrangement of first and second interdigitated electrodes separated by an insulating layer, where at least one gap extends therethrough. In one embodiment, interdigitated electrode assembly is a printed circuit board. An amount of medicament including at least one drug is then placed onto the interdigitated electrode assembly, step 1205, and the AC source cycles through at least two decades of frequencies, where the cycle comprises applying at least three frequencies per decade, step 1210. In one embodiment, the AC source is cycled through a range of frequencies from 0.1 Hz to 20,000 Hz. Current and phase information from the interdigitated electrode assembly at each frequency is monitored and collected, step 1215. Dielectric property information of the medicament as a function of frequency is calculated from the current and phase information using equations and relationships known in the art, step 1220. Dielectric property information is analyzed as a function of frequency or log of frequency, step 1225. An orienting frequency is selected to be a value where capacitance is relatively high and constant, step 1230. A motivating frequency is selected to be a value where conductivity is relatively high, step 1235. A signal having an orienting frequency and a signal having a motivating frequency are applied to the interdigitated electrode assembly, step 1240. In one embodiment, the orienting frequency is between about 0.1 Hz. and about 100 Hz. In one embodiment, the motivating frequency is between about 100 Hz. and about 20,000 Hz. In another embodiment, the signals may have an amplitude between about 1V to about 10V. In another embodiment, the interdigitated electrode arrangement and medicament are pre-packaged together in a bandage.

EXAMPLE 1

Experiments were performed to measure the transport of various active pharmaceutical agents through shedded snake skin and cow hoof barriers using a DEA 2970 Dielectric Analyzer v2.2A (TA Instruments). The DEA equipment comprises a furnace assembly configured to hold electrodes/sensors, allowing for measurement of certain dielectric characteristics of a substance at various temperatures.

Figure 13:
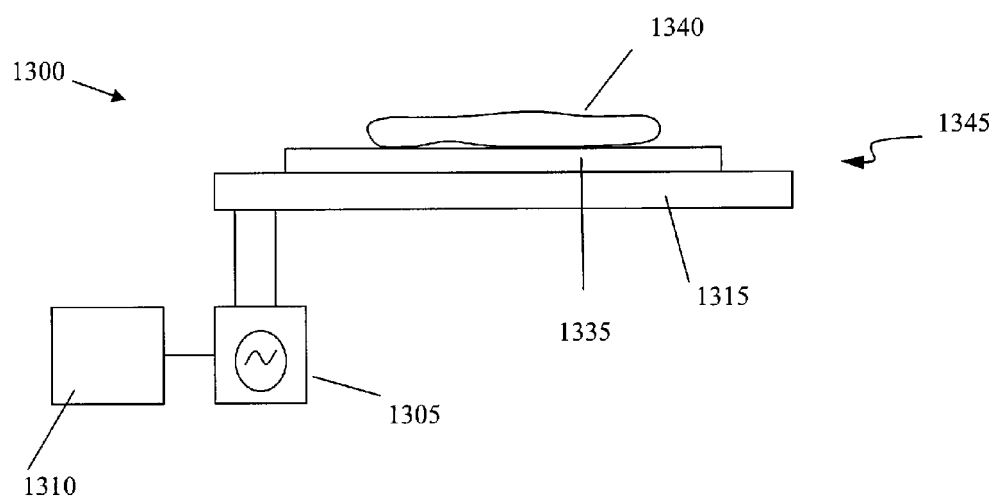
FIG. 13 is a side sectional view illustrating an experimental setup for use in analyzing the transport of drug through various membranes.

Referring to FIG. 13, the experimental setup 1300 comprises an AC signal generator 1305 combined with Universal Analysis v4.1D software (1310) electrically connected to a ceramic single-surface interdigitated electrode 1315. A sample of snake skin (reticulated python) 1335 is placed on the top surface of interdigitated electrode 1315 and an amount of Lamisil AT cream (active agent 1% terbinafine hydrochloride) 1340 is placed thereupon.

Figure 14:
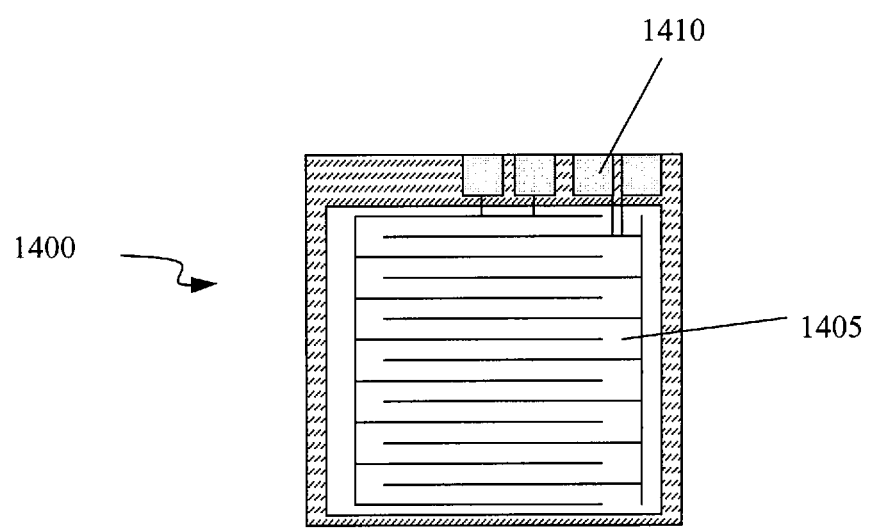
FIG. 14 is a perspective view illustrating an interdigitated electrode component of the experimental setup disclosed in FIG. 13.

Referring to FIG. 14, ceramic single-surface interdigitated electrode 1400 comprises a coplanar arrangement of ceramic substrate base, metal ground plate, and high temperature insulating layers and gold interdigitated electrodes components 1405 arranged thereupon. Interdigitated electrode components 1405 extend 0.013 mm above the ceramic substrate and are coplanar with it. The center-to-center distance between interdigitated electrodes components 1405 (excitation electrode to response electrode) is 254 micrometers. Electrical contact pads 1410 allow for electrical connection to a signal generator and data capture logic.

Again referring to FIG. 13, the entire arrangement 1345 is placed in the DEA furnace chamber and brought to 37° C. An AC signal is applied to interdigitated electrode 1315 at 1 Volt and the frequency is swept from 0.1 to 20,000 Hz for 120 minutes. Inspection of the arrangement 1345 following this protocol reveals a terbinafine hydrochloride residue on interdigitated electrode 1315. Identification of the residue was confirmed using a Varian 3900 gas chromatographer coupled to a Saturn 2000 mass spectrometer, using procedures well known in the art that involve comparing the mass spectra of the residue with the mass spectra of a known sample of terbinafine hydrochloride. Such a comparison reveals that the residue contains 94% of the terbinafine hydrochloride contained in the original sample—that is, 94% of the terbinafine hydrochloride in the Lamisil AT cream sample 1340 passes through a snake skin barrier 1335 at the aforementioned conditions. Similar analyses of Lamisil AT cream using cow hoof samples (0.75 in.$^2$×~1 mm.) in place of snake skin 1335 demonstrates that at least 73% of the terbinafine hydrochloride contained therein is motivated through cow hoof.

Control testing demonstrates that the transport of terbinafine hydrochloride through cow hoof samples is dramatically and unexpectedly enhanced by exposure to an AC field. Referring to FIG. 13, an initial control test comprises placing a cow hoof sample (0.75 in.$^2$×~1 mm.) onto the top surface of interdigitated electrode 1315 and placing an amount of Lamisil AT cream 1340 (active agent 1% terbinafine hydrochloride) onto the top surface of the cow hoof sample. The entire arrangement is placed in the DEA furnace and left at ambient temperature or brought to 37° C. No AC signal is applied. After 120 minutes, visual inspection reveals no residue on interdigitated electrode 1315, and therefore that no transport of terbinafine hydrocholride has occurred.

A second control test reveals that exposure to a DC field causes little, if any, transport of terbinafine hydrochloride. Referring to FIG. 13, a cow hoof sample (0.75 in.$^2$×~1 mm.) is placed onto the top surface of interdigitated electrode 1315 and an amount of Lamisil AT cream 1340 is placed onto the top surface of the cow hoof sample. The entire arrangement is placed in the DEA furnace and brought to 37° C. A DC signal is simulated by providing an AC signal to interdigitated electrode 1315 at a frequency of 0.001 Hz. At this frequency, each cycle runs for 50 minutes, and 2.4 cycles in total are provided during the 120 minute testing period. After such treatment, a small amount of residue is observed on interdigitated electrode 1315. Assuming that the entirety of the residue is composed of terbinafine hydrochloride, it is estimated that only 5-10% of the terbinafine hydrochloride present in the initial amount of Lamicil AT cream 1340 was transported through the cow hoof sample.

Table 1 summarizes the aforementioned results

TABLE 1

| Lamicil AT Cream (1% Terbinafine HCl) | | |
|---|---|---|
| | Residue Observed? | % Transported |
| AC Voltage: IV | | |
| Frequencies: 0.1 to 20,000 Hz | | |
| Time: 120 minutes | | |
| Shedded Snake Skin | Y | 94 |
| Cow Hoof | Y | 78 |
| Cow Hoof (repeat) | Y | 73 |
| Cow Hoof Controls | | |
| No signal, ambient T | N | |
| No signal, 37° C. | N | |
| simulated DC signal, 37° C. | Y | 5-10 |

Additional active pharmaceutical agents-including Ibuprofen, fluoxetine hydrocholoride (Prozac), ketoconazol (Nixoral), lidocaine, and norelgestromin (Ortho-Evera)—were tested on snake skin samples using the DEA equipment configuration and methodology noted above, with the exception that no gas chromatography/mass spectrometry confirmation analysis was performed. Providing an AC signal to interdigitated electrode 1315 in the manner outlined above resulted in buildup of residue on interdigitated electrode 1315 in every case, and thus confirmed that transport of material through snake skin had occurred.

EXAMPLE 2

Experiments were performed to measure the transport of terbinafine hydrochloride through shedded snake skin (reticulated python) and cow hoof samples using a printed circuit board (PCB) device. The basic design of the PCB may be illustrated by FIG. 5. That is, a first interdigitated electrode consisting of two complementary gold-plated copper "comb" electrode components is separated from a second, identical interdigitated electrode by an insulating layer containing interstitial areas that overlap those of the interdigitated electrodes. The PCB is about 1480×1500 mils with a 20 mil thickness and shows very good flexibility to conform to a non-planar surface.

The design of the remaining device components may be illustrated by FIG. 9. A small amount (~0.2 gram)of Lamicil AT (1% terbinafine hydrochloride) is placed on top of the PCB and a plate electrode is placed on top of the cream sample, with rubber spacers ensuring separation of the plate electrode from the PCB. A CH Instruments 660B Electrochemical Workstation potentiostat is utilized to generate the electrical signal. Electrical connections corresponding to each of Circuits 1-4 of FIG. 9 are made during testing, depending on the test sequence being run. That is, depending on the test sequence, an AC electrical signal is provided to the plate electrode and the first interdigitated electrode, which is shorted (Circuit 1), to the first interdigitated electrode, which was not shorted (Circuit 2), to the shorted first interdigitated electrode and the shorted second interdigitated electrode (Circuit 3), or to the second interdigitated electrode, which was not shorted (Circuit 4). Current data is collected and impedance information of the sample is calculated as a function of AC signal frequency.

Using the underlying principles of dielectrophoresis outlined above, the design of the equipment and testing protocol are based upon the idea that the use of relatively high frequency signal operates to motivate the active pharmaceutical agent (e.g., terbinafine hydrochloride), while the use of relatively low frequency signal operates to align or orient active pharmaceutical agents in the applied electric field, thereby increasing the effectiveness of any motivating high frequency signals. The use of relatively high frequency in Circuit 1 motivates active pharmaceutical agent in the surrounding medium toward the interdigitated electrode assembly, and the use of low, high, and low frequencies in Circuits 2, 3, and 4 orients the active pharmaceutical agent and further motivates it through the surrounding medium and into the membrane.

The following procedure was utilized to determine optimum high and low frequencies for transporting terbinafine hydrochloride contained in a Lamisil AT formulation. Testing is performed at room temperature, and at an AC amplitude of 2.25 Volts. The signal is first applied to Circuit 1 and frequency is cycled twice at a high frequency range (from 10,000 Hz to 100 Hz). Next, signal is applied to Circuit 2 and frequency is cycled twice at low frequency range (from 100 Hz to 0.10 Hz). Then, signal is applied to Circuit 3 and frequency is cycled twice at high frequency range. Finally, signal is applied to Circuit 4 and frequency is cycled twice at low frequency range. A plot of log(impedance) versus log(frequency) may provide indication of high and low frequencies that are favorable for transporting the terbinafine hydrochloride: a frequency is chosen in the high frequency range when impedance is relatively low (or alternatively, where conductivity is relatively high), whereas a frequency is chosen in the low frequency range when capacitance (or permittivity) is relatively high and constant. It is thought that a relatively constant capacitance indicates molecule alignment in the electric field.

Using the aforementioned procedure, frequencies of 0.5 Hz and 1225 Hz are chosen to utilize as low and high frequencies in assessing transport of terbinafine hydrochloride in Lamicil AT through shedded snake skin (reticulated python) and cow hoof (0.75 in.2×~1 mm.) samples. An AC signal is applied as follows, in order: 0.5 Hz for 30 minutes (Circuit 1); 1225 Hz for 30 minutes (Circuit 2); 0.5 Hz for 30 minutes (Circuit 3); 1225 Hz. for 30 minutes (Circuit 4). Visual inspection indicated residue on foil placed beneath the samples. Mass spectra indicate the transport of terbinafine hydrochloride through both snake skin and cow hoof samples.

EXAMPLE 3

Experiments were performed to measure the transport of various active pharmaceutical agents through pig skin using an interdigitated electrode assembly. The basic design of the assembly may be illustrated by FIG. 5. That is, a first interdigitated electrode consisting of two complementary stainless steel "comb" electrode components is separated from a second, identical interdigitated electrode by a virgin teflon insulating layer containing interstitial areas overlapping those of the interdigitated electrodes. The assembly is 0.75" (h)×0.91"(l)×0.12"(t) and is housed in a teflon cell. A pig skin sample is affixed beneath the second interdigitated electrode of the assembly. Samples of the active pharmaceutical agents are placed onto the first interdigitated electrode and a plate electrode covers the sample.

AC signal is provided to the assembly in the following general manner: two cycles at high frequency range (Circuit 1); two cycles at low frequency range (Circuit 2); two cycles at high frequency range (Circuit 3); two cycles at low frequency range (Circuit 4). Testing is performed at room temperature and at an AC amplitude of 3 Volts. Specific frequency ranges are listed in Table 2.

TABLE 2

Testing Schedule (Pig Skin)

| Sample | High Freq Range (Circuits 1 & 3) | Low Freq Range (Circuits 2 & 4) |
|---|---|---|
| Lidocaine | $10^7$-$10^4$ Hz | $10^4$-$10^{-1}$ Hz |
| Ibuprofein | $10^7$-$10^1$ Hz | $10^2$-$10^{-2}$ Hz |
| Ketoconasole | $10^7$-$10^4$ Hz | $10^2$-$10^{-2}$ Hz |
| Insulin | $10^7$-$10^2$ Hz | $10^2$-$10^{-1}$ Hz |
| Lamisil AT Cream | $10^7$-$10^4$ Hz | $10^2$-$10^{-1}$ Hz |

Conductivity of skin samples is measured before and after subjecting the samples to the aforementioned testing schedule. Results indicate that the conductivity of pig skin samples increased by 5-10 times after the testing schedule was applied. Increase in conductivity of pig skin samples is assumed to be an indicator of penetration of the active pharmaceutical agent into the sample. In contrast, a control was tested by applying the active pharmaceutical agents listed in Table 2 to pig skin samples for 1 hour, with no interdigitated electrode treatment, and conductivity measurements before and after application showed no change.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See Bryan A. Garner, *A Dictionary of Modern Legal Usage* 624 (2d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

While the present application has been illustrated by the description of embodiments thereof, and while the embodiments have been described in considerable detail, it is not the intention of the applicants to restrict or in any way limit the scope of the appended claims to such detail. For example, Methrotrexate is a drug with efficacy against warts. However, it is used only systemically since it does not penetrate skin layers. In another application of motivating substance into tissue, a transdermal patch with Methrotrexate may be effectively placed on a wart or other treatable skin condition, and then motivated to a treatment area below the skin surface. Existing treatment options are extremely painful since the drug is typically applied with syringes directly into the warts. Additional advantages and modifications will readily appear to those skilled in the art. Therefore, the application, in its broader aspects, is not limited to the specific details, representative apparatus, and illustrative examples shown and described. Accordingly, departures may be made from such details without departing from the spirit or scope of the applicant's general inventive concept.

What is claimed is:

1. A device for motivating a medicament through a membrane comprising:
    an alternating current (AC) signal source capable of providing an electric signal having an orienting frequency or an electric signal having a motivating frequency, or both;
    at least one non-uniform electrode electrically connected to the AC signal source, where the at least one non-uniform electrode comprises a first irregularly-shaped electrode and a second irregularly-shaped electrode, where the first and second irregularly-shaped electrodes are interdigitated electrodes; where the first and second irregularly-shaped electrodes are electrically connected to the AC signal source; where the first and second irregularly-shaped electrodes define at least one passage to allow an amount of the medicament to pass therethrough; where the first and second irregularly-shaped electrodes describe an equivalent circuit; and where the AC signal source applies an electric signal having an orienting frequency or an electric signal having a motivating frequency, or both, to the equivalent circuit.

2. The device of claim 1, where the orienting frequency and the motivating frequency are between 0.1 Hz and 20,000 Hz.

3. The device of claim 1, where the membrane is a biological membrane selected from the group consisting of skin, nail, and tooth tissue, and ocular, buccal, mucosal, vaginal, and rectal membrane.

4. The device of claim 1, where the medicament comprises a chemical compound selected from the group consisting of ACE inhibitors, steroids, analgesics, anti-coagulants, anti-arthritics, anti-infectives, anti-convulsants, anti-depressives, anti-fungals, anti-hypertensives, anti-psychotics, antihistamines, beta blockers, dermatologics, polypeptides, polynucleotides, NSAIDS, ocular drugs, hormones, and urology drugs, and any combination thereof.

5. The device of claim 1, where the first and second non-uniform electrodes are spaced apart from each other by an insulating layer having interstitial areas sufficient to allow an amount of the medicament to pass therethrough.

6. A patch for delivering a drug across a membrane, the patch comprising:
    connections for receiving an electrical signal having a motivating frequency, an orienting frequency, or both from an alternating current (AC) electrical power source;
    a bandage;
    a distal electrode disposed between the bandage and the membrane and adapted to be electrically connectable to at least one of the connections;
    at least one non-uniform electrode disposed proximate the distal electrode and the membrane, where the at least one non-uniform electrode comprises a first irregularly-shaped electrode and a second irregularly-shaped electrode, where the first and second irregularly-shaped electrodes are interdigitated electrodes; and where the first and second irregularly-shaped electrodes are each electrically connectable to respective ones of the connections;
    medicament disposed between the distal electrode and the at least one non-uniform electrode, the medicament comprising at least one drug;
    where the first and second irregularly-shaped electrodes define at least one passage to allow an amount of the at least one drug to pass therethrough;

where the distal electrode and the at least one non-uniform electrode describe a first equivalent circuit; and where the connections apply an electrical signal having an orienting frequency or an electric signal having a motivating frequency, or both, to the first equivalent circuit.

7. The patch as claimed in claim 6, where the at least one non-uniform electrode comprises a first and second non-uniform electrodes that are spaced apart from each other by an insulating layer having interstitial areas sufficient to allow an amount of the at least one drug to pass therethrough.

8. The patch as claimed in claim 7, where a second equivalent circuit is described by the first and second irregularly-shaped electrodes, and where the connections apply an electrical signal having an orienting frequency or an electric signal having a motivating frequency, or both, to the second equivalent circuit.

9. The patch as claimed in claim 7, where a second equivalent circuit is described by the first and second non-uniform electrodes, and where the connections apply an electrical signal having an orienting, frequency or an electric signal having a motivating frequency, or both, to the second equivalent circuit.

10. The patch as claimed in claim 7, comprising a second equivalent circuit, and where the connections apply an electrical signal having an orienting frequency or an electrical signal having a motivating frequency, or both, to the second equivalent circuit.

11. The patch as claimed in claim 6, where the medicament is selected from the group consisting of ACE inhibitors, steroids, analgesics, anti-coagulants, anti-arthritics, anti-infectives, anti-convulsants, anti-depressives, anti-fungals, anti-hypertensives, anti-psychotics, antihistamines, beta blockers, dermatologics, polypeptides, polynucleotides, NSAIDS, ocular drugs, hormones, and urology drugs, and any combination thereof.

* * * * *